United States Patent [19]

Gunkel

[11] Patent Number: 5,128,496
[45] Date of Patent: Jul. 7, 1992

[54] PROCESS FOR PREPARING STORAGE-STABLE TRIS(BROMOPHENYL)PHOSPHATES

[75] Inventor: Louis T. Gunkel, Yardley, Pa.

[73] Assignee: FMC Corporation, Philadelphia, Pa.

[21] Appl. No.: 706,132

[22] Filed: May 28, 1991

[51] Int. Cl.$^5$ ............................................. C07F 9/12
[52] U.S. Cl. .................................... 558/146; 558/211
[58] Field of Search .............................. 558/146, 211

[56] References Cited

U.S. PATENT DOCUMENTS

| | | | |
|---|---|---|---|
| 1,866,852 | 7/1932 | Hand et al. | 558/150 |
| 2,561,493 | 7/1951 | Caprio et al. | 106/177 |
| 2,894,015 | 7/1959 | Kyker | 260/461 |
| 3,436,441 | 4/1969 | Thompson | 260/966 |
| 3,526,681 | 9/1970 | English et al. | 260/949 |
| 3,945,891 | 3/1976 | Aal et al. | 203/77 |
| 4,059,655 | 11/1977 | Crano | 558/144 |
| 4,897,502 | 1/1990 | Gunkel et al. | 558/102 |

FOREIGN PATENT DOCUMENTS 50-47953 4/1975 Japan.
1168819 10/1969 United Kingdom.

OTHER PUBLICATIONS

Wiberg, K. B. Laboratory Technique in Organic Chemistry; McGraw-Hill, 1960; pp. 98–104.

Primary Examiner—Mary C. Lee
Assistant Examiner—Michael G. Ambrose
Attorney, Agent, or Firm—R. E. Elden; F. Ianno; R. L. Andersen

[57] ABSTRACT

The invention is a process for preparing a solid, storage-stable tris(bromophenyl)phosphate ester by the phosphorylation of a bromophenol and recovering the product by cooling a solution of the reaction mixture from a hydrocarbon solvent containing 2 to 20 parts of a C5 to C10 alkane per part of a C6 to C10 arene.

8 Claims, No Drawings

PROCESS FOR PREPARING STORAGE-STABLE TRIS(BROMOPHENYL)PHOSPHATES

The invention is a process for manufacturing storage-stable tris(bromophenyl)phosphate esters.

U.S. Pat. No. 3,945,891 to Aal et al. discloses that aryl phosphate esters are generally made by reacting an excess of a C1 to C4 alkyl phenol with phosphorus oxychloride in the presence of a catalyst, such as aluminum chloride or magnesium chloride. The patent discloses that increasingly more stringent limitations are being placed upon the allowable amount of unreacted and/or free phenols in the products. These requirements have created a demand for manufactured alkylated triaryl phosphate ester products containing less than the 500 to 3000 parts per million phenol previously available commercially.

U.S. Pat. No. 3,945,891 discloses alternative processes employed to remove any excess phenolics included caustic washing, permanganate oxidation, treatment with solid adsorbents and the like. Avoidance of these economically unattractive processing steps was achieved instead by an improved distillation process which could reduce the concentration of volatile phenol or alkylated phenol to 100 ppm.

U.S. Pat. No. 4,897,502 to Gunkel et al. discloses that a tri(haloaryl)phosphate ester that is a solid under ambient conditions usually is purified by recrystallization from an aromatic solvent such as toluene or xylene. Such a process is undesirable because the recrystallization steps are costly and the yield of product is reduced. The process usually necessitates further work up of crude product from the solvent mother liquor. Instead the patent teaches a process in which the reaction mixture is dissolved into an alcohol with a Hildebrand solubility parameter between 20 and 23 SI units and a Hansen dispersion coefficient between 14.2 and 15.5 SI units. On cooling, a pure solid product is recovered in high yield containing less than 100 ppm halophenol.

U.S. Pat. No. 2,561,493 discloses that solid chlorinated triphosphate esters can be recovered in a pure form by reacting the appropriate phenol with phosphorus oxychloride, distilling the product under vacuum, and recrystallizing the solid distillate by crystallizing from an equal volume of hexane or a mixture of ethylalcohol and acetone. However, this method is not satisfactory for tris(bromophenyl)phosphate esters because of their extreme insolubility in hexane and because they will transesterify in the presence of alcohols, increasing the halophenol concentration in the product.

On prolonged storage of a tris(bromophenyl)phosphate the strong odor of the corresponding bromophenol was found to develop, suggesting an unexpected decomposition of the product on storage. At other times the strong odor was noticed when the hot polymer mixture containing the product was molded.

The present invention is a process for preparing a solid, storage-stable tris(bromophenyl)phosphate ester by combining in a reactor about one mol of phosphorus oxyhalide, a catalytic amount of a Friedel-Crafts catalysr and about three mols of a bromophenol to form a reaction mixture, heating the reaction mixture sufficiently to maintain the reaction mixture as a liquid and to evolve hydrogen halide therefrom to provide a product that is solid when cooled to room temperature, incorporating the product into a sufficient quantity of a hydrocarbon solvent at an elevated temperature to form a dissolved reaction mixture, the hydrocarbon solvent consisting essentially of about 2 to about 20 parts by weight of a C5 to C10 alkane to each part by weight of a C6 to C10 arene selected from benzene or alkylbenzene, cooling the dissolved reaction mixture sufficiently to yield a solid phase in the dissolved reaction mixture, and separating the solid phase thereby providing a high yield of a purified solid tris(bromophenyl)phosphate containing less than 50 ppm bromophenol which is stable on storage.

The process is suitable for preparing any solid, tris(bromophenyl)phosphate, such as, tris(2-bromophenyl)phosphate, tris(3-bromophenyl)phosphate, tris(4-bromophenyl)phosphate, tris(2,4-dibromo-phenyl)phosphate, tris(2,4,6-tribromophenyl)phosphate, or the like. Preferably the process is useful for preparing tris(2,4-dibromophenyl)phosphate which is known to be useful as a flame retardant.

The reaction mixture can be incorporated into the hydrocarbon solvent after the reaction is completed, during the reaction or at the beginning of the reaction. Alternatively, either component of the hydro-carbon solvent may be added to the reaction mixture initially or during the reaction. For example, the reaction mixture could contain at least some of the alkane or arene which could assist in sweeping the hydrogen chloride out of the reactor on vaporizing, or alternatively, at least part of the arene or alkene could be incorporated into the reaction mixture, at or near the end of the reaction to assist in transferring the product from the reactor. The scope of the present invention is intended to include preparing the crude tris(bromophenyl)phosphate as an intermediate product and subsequently crystallizing the crude product in the hydrocarbon solvent.

For the purpose of this invention "storage-stable" or "stable on storage" means that the concentration of bromophenol will not increase to more than triple when stored 30 weeks at room temperature.

The proportions of alkane and arene can be varied over a wide range according to the alkane and arene employed and to the yield and purity desired for the tris(bromophenyl)phosphate product. For example, to obtain the maximum yield one would employ up to 20 parts by weight alkane per part of arene. On the other hand were the object to minimize the bromophenol content of the product, one skilled in the art might employ as little as two parts alkane per part by weight of alkylbenzene. When the alkane is heptane and the alkylbenzene is toluene a weight ratio of about 9 to 1 respectively (10% toluene by weight) provides an excellent compromise of purity and yield as it will form a saturated solution containing about 26% by weight of tris(2,4-dibromophenyl)phosphate. In general it is desirable for the saturated solution to contain at least about 15% and upto about 35% of the tris(bromophenyl)phosphate, preferably about 25% to 30%.

Clearly the desirable "elevated temperature" is a function of the alkane, arene and tris(bromophenyl)phosphate as well as the equipment being employed for the operations and can be determined by one skilled in the art without undue experimentation. Preferably, the temperature selected when the solvent is not to be recycled is sufficiently high to dissolve substantially all of the tris(bromophenyl)phosphate to form a solution that on cooling results in a maximum yield of purified tris(bromophenyl)phosphate. When the solvent is to be recycled obtaining the maximum yield per cycle is merely a desirable economic factor. When the dissolved reaction mixture is vented to the atmosphere, it is usually desirable if the temperature is maintained at or somewhat less than the reflux point of the mixture.

One skilled in the art will readily recognize that the boiling point of the alkane and arene may be a factor in selecting the optional hydrocarbon solvent mixture. Further, one skilled in the art will recognize that either the alkane, the arene, or both may be either a pure alkane or arene or a mixture of alkanes or arenes identified by boiling point.

Surprisingly, it was observed that the tris-(bromophenyl)phosphate made by the claimed process was more stable on storage than tris(bromophenyl)phosphate made by the process of copending patent application Ser. No. 706,133 filed May 28, 1991. It was also unexpectedly observed that the hydrocarbon solution containing the reaction mixture of the present process was less corrosive to stainless steel than the solution containing the reaction mixture of the copending application.

Although the invention is exemplified below in terms of the preferred tris(2,4-dibromophenyl)phosphate, it is not intended to limit the scope of the invention to that specific compound. Further, in order to minimize variables the process was divided into two steps, the phosphorylation reaction and the purification and separation of a storage-stable compound by means of a hydrocarbon solvent. However, one skilled in the art will recognize that the solvent could be incorporated into the reaction mixture ab initio, or that the crude product could be produced at one location and shipped to another location for the purification.

Preparation of crude tris(2,4-dibromophenyl)phosphate

A phosphorylation reaction was run by charging 1500 grams of 2,4-dibromophenol and 3.75 grams of magnesium chloride into a two-liter flask equipped with stirrer, thermometer, reflux condenser, heating mantle, and a caustic scrubber to absorb HCl by-product. This mixture was heated to 120° C. and 319.6 grams of phosphorus oxychloride were added over a two hour period. At the end of the phosphorus oxychloride addition, the mixture was heated to 160° C. and held for three and one-half hours. The end of the reaction was determined when the 2,4-dibromophenol remaining in the reaction mixture remained constant and the analysis showed the absence of any measurable amounts of partial phosphate esters, and chloridates. The analysis of the crude mixture showed 0.28% 2,4-dibromophenol and 99.4% ester product. A crude product weight of 1545 grams was obtained.

COMPARATIVE EXAMPLE A

Two hundred and fifty-five grams of the crude ester product above was dissolved in 726 grams of ethyl acetate at 75° C. to yield a clear solution. The mixture was then cooled slowly. At 50° C., crystals began to appear in the solution. When the temperature reached 25° C., the slurry was separated in a stainless steel centrifuge. Seven hundred and four grams of mother liquor were recovered which contained 0.06% 2,4-dibromophenol, 6.07% product and 0.34% chloridates.

The wet cake weighed 200 grams and the product dried to a weight of 192 grams. The product contained 14 ppm of 2,4-dibromophenol. Recovery from ethyl acetate was 75%.

EXAMPLE 1

Two hundred and forty-seven grams of the crude phosphorylation reaction mixture described above were dissolved into 704 grams of a mixed solvent solution consisting of 90 parts of commercial mixed heptanes and 10 parts toluene (a 90/10 mixture). The mix was heated to reflux (approximately 98° C.) in order to dissolve all the solids. The solution was then allowed to cool to 30° C. At this point the mixture consisted of a thick but free-flowing slurry of product crystals in the mixed solvent. This slurry was poured into a stainless steel basket centrifuge where the liquid and solids were separated. A mother liquor weighing 650 grams was recovered. The analysis of this solution showed 0.08% 2,4-dibromophenol and 0.03% other bromophenols as well as 0.1% chloridates and 1.54% product esters.

The wet cake weighed 231 grams and, after vacuum drying, the recovered product weight 223 grams. Gas chromatographic analysis of the product showed the level of 2,4-dibromophenol had been reduced to 37 ppm. Thus the crude product was recovered in better than a 95% yield in a crystalline form with the 2,4-dibromophenol levels being reduced from 0.238% in the crude to 37 ppm.

EXAMPLE 2

80/20 n-Heptane/Toluene Solvent

One hundred and thirty-eight grams of the crude tris(2,4-dibromophenyl)phosphate were dissolved in 392 grams of a 80/20 mixture of n-heptane and toluene at 90° C. The mix was cooled to room temperature whereupon a thick slurry of product and solvent were separated in a stainless steel basket centrifuge. Two hundred and sixty-nine grams of solvent were recovered as mother liquor from the separation. Evaporation and handling losses were high. This solution contained 2.4% solids consisting of 0.7% 2,4-dibromophenol, 0.4% chloridates, 0.26% 2,6 and 2,4,6 substituted bromophenols and 2.3% product.

The wet cake from the centrifuge weighed 120 grams and the vacuum dried final product weighed 117 grams and had a 2,4-dibromophenol content of 22 ppm. The recovered yield from the crude product was 85%.

EXAMPLE 3

85/15 n-Heptane/Toluene Solvent

Two hundred and eighty-four grams of crude tris-(2,4-dibromophenyl)phosphate were mixed with 808 grams of a solution of 85% n-heptane and 15% toluene as above. The liquid portion weighed 733 grams and contained 0.047% 2,4-dibromophenol, 1.45% ester product and 0.06% chloridates.

The wet cake weighed 266 grams and the product when dried weighed 254 grams. The material contained 36 ppm of 2,4-dibromophenol.

EXAMPLE 4

30 Week Storage

Two samples of crude tris(2,4-dibromophenyl)phosphate containing 0.28% 2,4-dibromophenol were recovered using (a) ethyl acetate and (b) a 90/10 mixture of heptane and toluene as previously described. The dibromophenol levels in the products immediately after drying were 10 and 8 ppm respectively. The samples were then stored in fiber pack storage containers and sampled over a 30 week period for dibromophenol analysis. The results are presented as Table I. This demonstrates the unexpected storage stability of the product made by the claimed process.

EXAMPLE 5

Corrosion Studies

At the end of the reaction step to make tris(2,4-tribromophenyl)phosphate the crude reaction mixture contains some dissolved HCl by-product in addition to excess 2,4-dibromophenol, chloridates and product. It was observed that when ethyl acetate was the solvent there was unexpected corrosion attack on any stainless steel equipment that came into contact with this solution. In order to determine the corrosivity the mother liquors of the two solvent systems were dried with molecular sieves to a moisture content of less than 30 ppm $H_2O$. Samples of the stainless steel were then exposed to solutions of these solvents that were used to work up portions on the same crude reaction mixtures. The slurry mixtures represented material that was ready to be sent to the centrifuge.

The 316 ss test strip exposed to the ethyl acetate solution at 70° C. evidenced a corrosion rate of 20 mils per year, which is unacceptable. The mixed solvent solution showed a corrosion rate of only 1-2 mils per year at 70° C., which is an acceptable rate.

EXAMPLE 6

Solvent Recycle

A quantity of crude tris(2,4-dibromophenyl)phosphate was prepared with a final composition of 0.6% 2,4-dibromophenol, <0.01% 2,4,6-tribromophenol, a trace of the chloridate intermediate product, bis-(2,4-dibromophenyl), chlorophosphate, and the remainder the product ester. This crude product was divided into six portions. The first portion was crystallized or worked up from fresh quantity of the 90/10 mixed heptane/toluene solvent. The subsequent portions were worked up with the same solvent, with the exception that some additional small amount of fresh solvent had to be added to each recycle batch to make up for solvent lost during the recovery of the product.

The procedure was to add the crude product to the solvent mix to a concentration of 26%. The mixture was then heated to about the reflux point of the solvent mix, (88° C.) whereupon the crude product dissolved. The mixture was then allowed to cool with stirring. The solution was cooled to 25° C. and then filtered in a basket centrifuge. The recovered solvent was weighed, analyzed and prepared for reuse. The product was dried in a vacuum oven and analyzed for dibromophenol content. Table II shows the material balance of the six recycle tests. Table III shows the analysis of the recovered solvents (mother liquors) after each cycle.

The analysis of the recycle solvent solution shows an increase in the impurities levels as the recycle steps continue, demonstrating that the mixed solvent is successful in removing these impurities. The analysis of the final, dried product (Table II) shows the levels of the undesired 2,4-dibromophenol remain low over all five recycle runs.

TABLE I

DIBROMOPHENOL (DBP) BUILD-UP IN TRIS(2,4-DIBROMOPHENYL) PHOSPHATE RECOVERED WITH ETHYL ACETATE AND 90:10 HEPTANE/TOLUENE

| Sample After Weeks | PPM DBP | |
|---|---|---|
| | A Ethyl Acetate | B 90:10 Heptane/Toluene |
| 0 | 10 | 8 |
| 4 | 40 | 10 |
| 8 | 47 | 10 |
| 12 | 50 | 10 |
| 28 | 69 | 20 |

TABLE II

MATERIAL BALANCE ON RECYCLE

| | Cycle No. | | | | | |
|---|---|---|---|---|---|---|
| | 1 | 2 | 3 | 4 | 5 | 6 |
| Wt. Product Grams | 187.5 | 189.5 | 176.1 | 209.0 | 194.7 | 179.5 |
| Wt. Solvent Fresh, grams | 534 | 78 | 47 | 170 | 45 | 30 |
| Wt. Solvent Recycled, grams | 0 | 461 | 454 | 425 | 509 | 481 |
| Recovered Solvent, grams | 473 | 481 | 456 | 540 | 508 | 441 |
| Recovered Product, Wet | 184.7 | 187.9 | 167.9 | 212.7 | 191.7 | 191.3 |
| Recovered Product, Dry | 171.8 | 162.8 | 162.8 | 191.7 | 171.3 | 179.5 |
| 2,4-DBP Content, ppm | 49 | 11 | 13 | 12 | 14 | 48 |

TABLE III

ANALYSIS OF RECYCLED SOLVENT

| | Cycle No. | | | | | |
|---|---|---|---|---|---|---|
| | 1 | 2 | 3 | 4 | 5 | 6 |
| Grams 2,4-DBP | .420 | .428 | .515 | .528 | .745 | .853 |
| Grams 2,4,6-DBP | .086 | .090 | .109 | .140 | .189 | .203 |
| Grams Chloridate | .018 | .101 | .513 | .866 | .891 | 1.10 |
| Grams Product | 6.8 | 6.5 | 9.7 | 11.6 | 10.6 | 12.3 |

I claim:

1. A process for preparing a solid, storage-stable tris(-bromophenyl)phosphate ester comprising combining in a reactor about one mol of phosphorus oxyhalide, a catalytic amount of a Friedel-Crafts catalyst and about three mols of a bromophenol to form a reaction mixture, heating the reaction mixture sufficiently to maintain the reaction mixture as a liquid and to evolve hydrogen halide therefrom to provide a product which is solid when cooled to room temperature, incorporating the product into a sufficient quantity of a hydrocarbon solvent at an elevated temperature to form a dissolved reaction mixture, the hydrocarbon solvent consisting essentially of about 2 to about 20 parts by weight of a C5 to C10 alkane to each part by weight of a C6 to C10 arene selected from benzene or alkylbenzene, cooling the dissolved reaction mixture sufficiently to yield a solid phase in the dissolved reaction mixture, and separating the solid phase thereby providing a high yield of a purified solid tris(bromophenyl)phosphate which is stable on storage.

2. The process of claim 1 wherein the hydrocarbon solvent consists essentially of about 10 parts by weight alkane and about 1 part by weight arene.

3. The process of claim 1 wherein the hydrocarbon solvent consists essentially of heptane and toluene.

4. The process of claim 2 wherein the hydrocarbon solvent consists essentially of heptane and toluene.

5. The process of claim 1 wherein at least part of the hydrocarbon solvent is incorporated into the reaction mixture in the reactor.

6. The process of claim 2 wherein at least part of the hydrocarbon solvent is incorporated into the reaction mixture in the reactor.

7. The process of claim 3 wherein at least part of the hydrocarbon solvent is incorporated into the reaction mixture in the reactor.

8. The process of claim 4 wherein at least part of the hydrocarbon solvent is incorporated into the reaction mixture in the reactor.

* * * * *